United States Patent
Dubay et al.

(10) Patent No.: US 10,851,063 B2
(45) Date of Patent: Dec. 1, 2020

(54) METHODS FOR PREPARING LEVORPHANOL AND RELATED COMPOUNDS, AND COMPOSITIONS THEREOF

(71) Applicant: AMPAC Fine Chemicals LLC, Rancho Cordova, CA (US)

(72) Inventors: William Dubay, Folsom, CA (US); Alex Nichols, Madison, WI (US); Wei Chen, Folsom, CA (US); Alec Brozell, San Francisco, CA (US); Ajay Ryerson, Sacramento, CA (US)

(73) Assignee: AMPAC FINE CHEMICALS LLC, Rancho Cordova, CA (US)

( * ) Notice: Subject to any disclaimer, the term of this patent is extended or adjusted under 35 U.S.C. 154(b) by 0 days.

(21) Appl. No.: 16/151,798

(22) Filed: Oct. 4, 2018

(65) Prior Publication Data

US 2020/0109119 A1  Apr. 9, 2020

(51) Int. Cl.
*C07D 221/28* (2006.01)
*C07C 59/255* (2006.01)

(52) U.S. Cl.
CPC .......... *C07D 221/28* (2013.01); *C07C 59/255* (2013.01); *C07B 2200/13* (2013.01)

(58) Field of Classification Search
CPC .................................................. C07D 221/28
See application file for complete search history.

(56) References Cited

U.S. PATENT DOCUMENTS

| | | | |
|---|---|---|---|
| 2,524,855 A | 10/1950 | Schnider et al. | |
| 2,744,112 A | 5/1956 | Vogler | |
| 3,634,429 A | 1/1972 | Leimgruber et al. | |
| 4,521,601 A | 6/1985 | Rice | |
| 4,727,147 A | 2/1988 | Wintermeyer et al. | |
| 5,892,044 A | 4/1999 | Werbitzky | |
| 9,861,629 B1* | 1/2018 | Hughey | A61K 9/4833 |
| 2008/0146805 A1* | 6/2008 | Haar | C07D 221/28 546/74 |

OTHER PUBLICATIONS

Kumaraguru et al., "An Improved Process for the Preparation of (+)-3-Methoxy-N-formylmorphinan," Organic Process Research and Development, vol. 18, pp. 174-178 (2014).

* cited by examiner

*Primary Examiner* — Svetlana M Ivanova
(74) *Attorney, Agent, or Firm* — Ice Miller LLP (57) ABSTRACT

A method for producing substantially pure levorphanol and related compounds, when compared to the conventional process, is provided. In particular, a method for producing substantially pure levorphanol tartrate dihydrate is described. Also described are compositions comprising levorphanol and related compounds, particularly compositions comprising levorphanol tartrate dihydrate, levomethorphan, and norlevorphanol in which the levomethorphan and norlevorphanol are present in the composition in reduced levels.

4 Claims, 3 Drawing Sheets

METHODS FOR PREPARING LEVORPHANOL AND RELATED COMPOUNDS, AND COMPOSITIONS THEREOF

FIELD OF THE INVENTION

The invention relates to methods for preparing substantially pure levorphanol and related compounds, and compositions thereof. In particular, the invention relates to methods for preparing compositions of levorphanol having reduced levels of impurities by reacting levorphanol with ethyl formate, forming a salt with an acid, and crystallizing the formed salt.

BACKGROUND OF THE INVENTION

Levorphanol (CAS No.: 77-07-6), levorphanol tartrate (CAS No.: 125-72-4), and levorphanol tartrate dihydrate (CAS No.: 5985-38-6) are well known narcotic opioid analgesics that belong to a class of chemical compounds known as morphinans. Structures of these compounds are shown below:

Levorphanol x = 0, Levorphanol tartrate
x = 2, Levorphanol tartrate dihydrate

Levorphanol and related compounds are conventionally prepared from levomethorphan hydrobromide. In particular, levomethorphan is treated with aqueous hydrobromic acid (HBr) for the demethylation to produce an aqueous HBr solution of levorphanol. Then the resulting HBr solution is neutralized with ammonium hydroxide ($NH_4OH$) to form crude levorphanol. The crude levorphanol formed can be converted to anhydrous levorphanol or reacted with aqueous tartaric acid to form levorphanol tartrate or levorphanol tartrate dihydrate.

One of many challenges with the conventional production process is to minimize or eliminate the presence of impurities. As levorphanol, levorphanol tartrate, and levorphanol tartrate dihydrate are prescribed as drugs, it is important to obtain these compounds in highly pure forms, which contain minimal levels of impurities.

Therefore there is a need to develop new processes that reduce or eliminate the impurities produced by the conventional processes used to synthesize levorphanol, levorphanol tartrate, and levorphanol tartrate dihydrate, as well as methods to analyze and determine the purity thereof.

BRIEF SUMMARY OF THE INVENTION

The invention is directed to compositions and methods for preparing levorphanol, and particularly levorphanol tartrate dihydrate in substantially pure form as compared to other methods known in the art for preparing levorphanol. In particular, the invention relates to a composition comprising levorphanol tartrate dihydrate, levomethorphan, and norlevorphanol, and methods of preparing such compositions.

In one general aspect, the invention relates to a composition comprising levorphanol tartrate dihydrate, levomethorphan, and norlevorphanol, wherein the composition comprises levomethorphan in an amount that is about 0.5% area or less based on peak area of a peak corresponding to levomethorphan as determined by high performance liquid chromatography (HPLC) analysis relative to a total of 100% area based on peak area of peaks corresponding to levorphanol tartrate dihydrate, levomethorphan, and norlevorphanol as determined by HPLC analysis, and norlevorphanol in an amount that is about 0.5% area or less based on peak area of a peak corresponding to norlevorphanol as determined by HPLC analysis relative to a total of 100% area based on peak area of peaks corresponding to levorphanol tartrate dihydrate, levomethorphan, and norlevorphanol as determined by HPLC analysis.

In one embodiment, a composition described herein comprises levomethorphan in an amount that is about 0.3% area or less, preferably 0.2% area or less, and more preferably 0.15% area or less, based on peak area of a peak corresponding to levomethorphan as determined by high performance liquid chromatography (HPLC) analysis relative to a total of 100% area based on peak area of peaks corresponding to levorphanol tartrate dehydrate, levomethorphan, and norlevorphanol as determined by HPLC analysis.

In one embodiment, a composition described herein comprises norlevorphanol in an amount that is about 0.3% area or less, preferably 0.2% area or less, and more preferably 0.15% area or less, based on peak area of a peak corresponding to norlevorphanol as determined by high performance liquid chromatography (HPLC) analysis relative to a total of 100% area based on peak area of peaks corresponding to levorphanol tartrate dehydrate, levomethorphan, and norlevorphanol as determined by HPLC analysis.

In a preferred embodiment, a composition described herein comprises each of levomethorphan and norlevorphanol in an amount that is about 0.15% area or less based on peak area of the peaks corresponding to levomethorphan and norlevorphanol, respectively In another general aspect, the invention relates to a method of preparing a composition comprising levorphanol tartrate dihydrate, levomethorphan, and norlevorphanol. In particular, the method comprises:
(i) reacting levorphanol tartrate with a base to obtain a mixture;
(ii) reacting the mixture with ethyl formate to obtain a second mixture;
(iii) reacting the second mixture with L-(+)-tartaric acid to obtain a third mixture comprising levorphanol tartrate; and
(iv) crystallizing the levorphanol tartrate from the third mixture in an aqueous-organic solvent mixture to obtain the composition.

In another general aspect, the invention relates to a method of determining an amount of an impurity in a composition comprising levorphanol tartrate dihydrate, the method comprising:
(i) dissolving the composition in a suitable solvent to prepare a sample solution;
(ii) dissolving a reference standard of levorphanol tartrate dihydrate in a solvent to prepare a standard solution;
(iii) analyzing the sample solution and the standard solution by high performance liquid chromatograph (HPLC) to identify a peak corresponding to levorphanol tartrate dihydrate and the impurity;
(iv) measuring an area of the peak corresponding to levorphanol tartrate dihydrate and an area of the peak corresponding to the impurity; and
(v) determining the amount of the impurity based on the peak area from step (iv).

In certain embodiments, the impurity is at least one of levomethorphan and norlevorphanol.

In yet another general aspect, the invention relates to a method of treating pain in a subject in need thereof, the method comprising administering to the subject a composition as described herein.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Unless defined otherwise, all technical and scientific terms used herein have the same meaning as is commonly understood by one of ordinary skill in the art to which this invention pertains. Otherwise, certain terms used herein have the meanings as set in the specification. All patents, published patent applications and publications cited herein are incorporated by reference as if set forth fully herein.

All publications and patents referred to herein are incorporated by reference. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, an amount of about 0.5% area or less includes 0.45% to 0.55% area. As used herein, the use of a numerical range expressly includes all possible subranges, all individual numerical values within that range, including integers within such ranges and fractions of the values unless the context clearly indicates otherwise.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having."

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "substantially pure" when used in reference to a particular compound refers to the compound where it is substantially free of impurities, e.g., isolated from a composition where other chemical components are co-isolated therewith. Preferably, the analytical purity of a compound as determined by high performance liquid chromatography (HPLC) is at least 70%, more preferably at least 90%; and even more preferably at least 95%, such as 96%, 97%, 98%, 99%, 99.1%, 99.2%, 99.3%, 99.4%, 99.5%, 99.6%, 99.7%, 99.8%, 99.9% or 100%. As used herein with respect to a composition comprising levorphanol tartrate dihydrate, the term "substantially pure" refers to an analytical purity of levorphanol tartrate dihydrate in the composition that is preferably at least 99.0%, and more preferably 99.6% or 99.7% or greater as determined by HPLC. Typical impurities in a composition comprising levorphanol tartrate dihydrate include levomethorphan and norlevorphanol.

Conventional processes for the production of levorphanol, levorphanol tartrate, and levorphanol tartrate dihydrate start with levomethorphan, which can be prepared from reduction of formyl-levomethorphan. In particular, demethylation of levomethorphan is achieved with aqueous hydrobromic acid (HBr) to produce an aqueous HBr solution of levorphanol. The resulting HBr is neutralized with ammonium hydroxide (NH$_4$OH) and extracted with a mixture of chloroform and isopropanol. The levorphanol ends up in the organic layer and can be extracted. To prepare levorphanol tartrate, crude solid levorphanol is dissolved in an alcohol solvent, typically isopropanol, and tartaric acid is added. Crystallization of levorphanol tartrate from aqueous isopropanol affords levorphanol tartrate dihydrate. This process is disclosed in, e.g., U.S. Patent Application Publication No. 2008/0146805 A1. This conventional process for preparing levorphanol tartrate, which can then be crystallized from aqueous isopropanol to afford levorphanol tartrate dihydrate, is shown in Scheme 1 below.

Scheme 1: Process for Preparing Levorphanol Tartrate from Formyl-Levomethorphan

Levorphanol tartrate

A disadvantage associated with the above-described conventional process is that the resulting final products of levorphanol tartrate and levorphanol tartrate dihydrate contain several undesirable impurities, such as norlevorphanol, which originates from the step of reduction of formyl-levomethorphan. Once these impurities are generated in the conventional synthetic processes, they became incorporated into the final products unless removed by purification. However, standard recrystallization processes often fail to remove these impurities from the final products or at least reduce the level of these impurities to below a certain amount. For example, norlevorphanol, one impurity present in the crude levorphanol, is difficult to remove from levorphanol tartrate by crystallization.

Another impurity often present in the final products of levorphanol tartrate and levorphanol tartrate dehydrate is the levomethorphan starting material, which results from the incomplete demethylation of levomethorphan in aqueous HBr. The structures of levomethorphan and norlevorphanol are shown below:

Levomethorphan                    Norlevorphanol

The inventors of the invention have discovered that additional purification steps added to the conventional process of producing levorphanol tartrate dihydrate can reduce the amount of impurities, particularly the amount of norlevorphanol and levomethorphan to provide levorphanol tartrate dihydrate with improved purity.

Thus, in one general aspect, the invention relates to a method of preparing a composition comprising levorphanol tartrate dihydrate. In particular, the method comprises:
  (i) reacting levorphanol tartrate with a base to obtain a mixture;
  (ii) reacting the mixture with ethyl formate to obtain a second mixture;
  (iii) reacting the second mixture with L-(+)-tartaric acid to obtain a third mixture comprising levorphanol tartrate; and
  (iv) crystallizing the levorphanol tartrate from the third mixture in an aqueous-organic solvent mixture to obtain the composition.

The method described herein effectively removes common impurities in levorphanol tartrate dihydrate preparations, particularly norlevorphanol.

In another general aspect, the invention relates to a composition comprising levorphanol tartrate dihydrate produced by a method of the invention. Compositions comprising levorphanol tartrate dihydrate prepared according to the methods described herein can further comprise levomethorphan and norlevorphanol. Preferably, the levomethorphan and norlevorphanol are present in reduced amounts as compared to the amount in compositions comprising levorphanol tartrate dihydrate prepared according to conventional methods.

According to embodiments of the invention, a composition prepared by the method described herein comprises substantially pure levorphanol tartrate dihydrate, meaning that the amount of levorphanol tartrate dihydrate present in the composition relative to impurities, namely levomethorphan and norlevorphanol is at least 95%, such as at least 96%, 97%, 98%, or 99%, preferably at least 99%, more preferably at least 99.1%, 99.2%, 99.3%, 99.4%, 99.5%, 99.6%, 99.7%, 99.8%, or 99.9% or greater. The purity of levorphanol tartrate dihydrate can be determined by analytical methods, preferably high performance liquid chromatography (HPLC).

In certain embodiments, the levorphanol tartrate used in step (i) of the method described herein can be crude levorphanol tartrate. As used herein, "crude levorphanol tartrate" refers to the product obtained from a reaction of levorphanol and L-(+)-tartaric acid before any crystallization step. Levorphanol and crude levorphanol can be obtained by any method known in the art in view of the present disclosure. For example, levorphanol can be obtained by demethylation of levomethorphan in aqueous HBr followed by neutralization with ammonium hydroxide and extraction with a mixture of chloroform and isopropanol. Levomethorphan can be synthesized by any method known in the art in view of the present disclosure. The obtained levorphanol can be reacted with tartaric acid, particularly L-(+)-tartaric acid, to obtain crude levorphanol tartrate, which can be used directly in the methods of the invention described herein.

In certain embodiments, the base used in the step (i) of the method described herein includes an organic base or an inorganic base, wherein the organic base is preferably triethylamine, diethylamine, N,N-diisopropylethylamine, or pyridine, or any combination thereof, and the inorganic base is preferably lithium hydroxide, sodium hydroxide, potassium hydroxide, sodium carbonate, sodium bicarbonate, potassium carbonate, potassium bicarbonate or cesium carbonate, or any combination thereof. Preferably, the base is an inorganic base, and is more preferably sodium carbonate, sodium bicarbonate, potassium carbonate, or potassium bicarbonate, most preferably sodium carbonate.

According to embodiments of the invention, reaction of crude levorphanol tartaric acid with a base produces a mixture comprising levorphanol (free base) and norlevorphanol. Reaction of this mixture with ethyl formate produces formylated norlevorphanol. Thus, in certain embodiments, the second mixture obtained in step (ii) of the method described herein comprises formylated norlevorphanol. Reaction of this second mixture with L-(+)-tartaric acid produces a third mixture comprising levorphanol tartrate. In certain embodiments, the third mixture obtained in step (iii) further comprises formylated norlevorphanol and any norlevorphanol that is unreacted with the ethyl formate.

According to embodiments of the invention, the mixture comprising levorphanol (free base) and norlevorphanol produced from base treatment of crude levorphanol tartaric acid can be separated, and the aqueous phase extracted with ethyl formate. Ethyl formate can then be added to the organic phase to produce formylated norlevorphanol. In some embodiments, about [range of mole or weight ratio of ethyl formate] of ethyl formate is added. The resulting mixture is then heated to a temperature of about 50° C. to 65° C., preferably about 55° C. to 60° C., for instance about 57° C. The reaction is allowed to proceed until completion, which can be determined by, for example, monitoring the reaction by HPLC. In a typical embodiment, the reaction with ethyl formate is allowed to proceed for about 1 to 10 hours, such as 1, 2, 3, 4, 5, 6, 7, 8, 9, or 10 hours, more preferably about four hours.

According to embodiments of the invention, levorphanol tartrate is crystallized from the third mixture in an aqueous-organic solvent mixture to obtain a composition comprising levorphanol tartrate dihydrate. In certain embodiments, the aqueous-organic mixture comprises a solvent selected from the group consisting of methanol, ethanol, propanol, and isopropyl alcohol or a mixture thereof, preferably isopropyl alcohol.

Once the reaction is complete, the levorphanol tartrate in step (iii) or the levorphanol tartrate dihydrate in step (iv) can be recovered from the reaction mixture. Methods for recovering such compounds from the reaction mixture are not particularly limited, and any method known in the art in view of the present disclosure can be used to isolate the compound, such as distillation, filtration, crystallization, precipitation, etc. For example, after the salt formation at elevated temperature, the reaction mixture can be slowly cooled down to room temperature or lowered to precipitate out the formed solid. The precipitated solid can be filtered, washed and dried. One of ordinary skill in the art will readily be able to determine and employ the appropriate techniques for recovering levorphanol tartrate in step (iii) or the levorphanol tartrate dihydrate in step (iv) from the reaction mixture in order to maximize compound yield, purity, etc.

Further purification of levorphanol, levorphanol tartrate, or levorphanol tartrate dihydrate can be achieved by recrystallization. Any water soluble organic solvent may be used for recrystallization, including acetonitrile, acetone and other water soluble ketones, water soluble alcohols, tetrahydrofuran (THF) and other water soluble ethers, diglyme and other glymes, and mixtures of the same. Examples of suitable alcohols include methyl alcohol, ethyl alcohol, n-propyl alcohol, n-butyl alcohol, iso-butyl alcohol, tertiary butyl alcohol, n-pentyl alcohol, iso-pentyl alcohol, and neo-pentyl alcohol. Preferably, the alcohol is used as a solution in water, i.e., an aqueous alcohol, in which the concentration of alcohol in the solution is greater than 80% (w/w). The recrystallization of levorphanol tartrate dihydrate from the anhydrous form is preferably conducted in water. However, other solvents or solvent mixtures can be used as long as they yield the product with the desired purity, yield and degree of hydration. For example, a water and alcohol mixture in which the concentration of alcohol in the mixture is about 75% (w/w) or less can be used for the recrystallization of levorphanol tartrate dihydrate.

A method of preparing a composition comprising levorphanol tartrate dihydrate, according to embodiments of the present invention is depicted in Scheme 2 below. Levorphanol tartrate, which contains some level of norlevophanol impurity is treated with base to generate levorphanol (free base). Base treatment typically does not produce any additional norlevorphanol. The resulting mixture is then treated with ethyl formate, followed by tartaric acid and purified as described above to obtain a composition comprising levorphanol tartrate dihydrate. Such compositions can further comprise norlevorphanol and levomethorphan, although the amount of these impurities present in the composition is lower as compared to the amount of these impurities in compositions prepared according to conventional methods.

In yet another general aspect, the present invention relates to a composition comprising levorphanol tartrate dihydrate, levomethorphan, and norlevorphanol. Such compositions can be prepared by any of the methods described herein for preparing compositions comprising levorphanol tartrate dihydrate.

According to embodiments of the invention, a composition comprises levomethorphan in an amount that is about 0.5% area or less based on peak area of a peak corresponding to levomethorphan as determined by high performance liquid chromatography (HPLC) analysis relative to a total of 100% area based on peak area of peaks corresponding to levorphanol tartrate dihydrate, levomethorphan, and norlevorphanol as determined by HPLC analysis, and norlevorphanol in an amount that is about 0.5% area or less based on peak area of a peak corresponding to norlevorphanol as determined by HPLC analysis relative to a total of 100% area based on peak area of peaks corresponding to levorphanol tartrate dihydrate, levomethorphan, and norlevorphanol as determined by HPLC analysis In one embodiment, a composition described herein comprises levomethorphan in an amount that is about 0.5% area or less based on peak area of a peak corresponding to levomethorphan as determined by high performance liquid chromatography (HPLC) analysis relative to a total of 100% area based on peak area of peaks corresponding to levomethorphan, norlevorphanol, and levorphanol tartrate dihydrate as determined by HPLC analysis. For example, a composition comprises levomethorphan in an amount that is about 0.5%, 0.4%, 0.3%, 0.2%, 0.15%, 0.1%, 0.05%, 0.02%, or 0.01% area or less, based on peak area of a peak corresponding to the levomethorphan as determined by high performance liquid chromatography (HPLC) analysis, relative to a total of 100% area based on peak area of peaks corresponding to levomethorphan, norlevorphanol, and levorphanol tartrate dihydrate as determined by HPLC analysis. Preferably, a composition comprises levomethorphan in an amount that is about 0.2% area or less, more preferably 0.15% area or less based on a peak area of the peak corresponding to levomethorphan.

In one embodiment, a composition comprises norlevorphanol in an amount that is about 0.5% area or less based on peak area of a peak corresponding to norlevorphanol as determined by high performance liquid chromatography (HPLC) analysis relative to a total of 100% area based on peak area of peaks corresponding to the levomethorphan, norlevorphanol, and levorphanol tartrate dihydrate as determined by HPLC analysis. For example, a composition comprises norlevorphanol in an amount that is about 0.5%, 0.4%, 0.3%, 0.2%, 0.15%, 0.1%, 0.05%, 0.02%, or 0.01% area or less, based on peak area of a peak corresponding to the norlevorphanol as determined by high performance liquid chromatography (HPLC) analysis, relative to a total of 100% area based on peak area of peaks corresponding to levomethorphan, norlevorphanol, and levorphanol tartrate dihydrate as determined by HPLC analysis. Preferably, a composition comprises norlevorphanol in an amount that is about 0.2% area or less, more preferably 0.15% area or less based on a peak area of the peak corresponding to norlevorphanol.

In a particular embodiment, a composition comprises each of levomethorphan and norlevorphanol in an amount that is at about 0.2% area or less, more preferably 0.15% area or less based on peak area of the peaks corresponding to levomethorphan and norlevorphanol, respectively, as determined by HPLC analysis.

In a particular embodiment, a composition comprising levorphanol tartrate dihydrate is obtained by a method comprising:
(i) reacting levorphanol tartrate with a base to obtain a mixture;
(ii) reacting the mixture with ethyl formate to obtain a second mixture;
(iii) reacting the second mixture with L-(+)-tartaric acid to obtain a third mixture comprising levorphanol tartrate; and
(iv) crystallizing the levorphanol tartrate from the third mixture an aqueous-organic solvent mixture to obtain the composition.

The composition can further comprise levomethorphan and/or norlevorphanol each in an amount that is 0.5% or less, preferably about 0.2% area or less, more preferably 0.15% area or less based on peak area of the peaks corresponding to levomethorphan and norlevorphanol, respectively, as determined by HPLC analysis.

According to embodiments of the invention, one or more impurities in a composition comprising levorphanol tartrate or levorphanol tartrate dihydrate can be determined by HPLC. High performance liquid chromatography (HPLC) is a chromatographic separation technique in which high-pressure pumps force the substance or mixture being analyzed together with a mobile phase, also referred to as the eluent, through a separating column containing the stationary phase. HPLC analysis can be performed in isocratic mode or gradient mode. In an isocratic mode, the mobile phase composition is constant throughout. In contrast, a gradient HPLC mode is carried out by a gradual change over a period of time in the percentage of the two or more solvents making up the mobile phase. The change in solvent is controlled by a mixer which mixes the solvents to produce the mobile phase prior to its passing through the column.

In a particular embodiment, an HPLC method for determining and quantifying the amount of impurities in a composition comprising levorphanol tartrate or levorphanol tartrate dihydrate, comprises:
(i) dissolving the composition in a suitable solvent to prepare a sample solution;
(ii) dissolving a reference standard of levorphanol tartrate or levorphanol tartrate dihydrate in a solvent to prepare a standard solution;
(iii) analyzing the sample solution and the standard solution by high performance liquid chromatograph (HPLC) to identify a peak corresponding to levorphanol tartrate or levorphanol tartrate dihydrate and the impurity;
(iv) measuring an area of the peak corresponding to levorphanol tartrate or levorphanol tartrate dihydrate and an area of the peak corresponding to the impurity; and
(v) determining the amount of the impurity based on the peak areas from step (iv).

In one embodiment, an impurity is levomethorphan.

In another embodiment, an impurity is norlevorphanol.

In other embodiments, impurities are levomethorphan and norlevorphanol.

In some embodiments, the mobile phase A is a phosphate buffer solution, mobile phase B is a mixture of acetonitrile and methanol, and diluent is water.

In a certain embodiment, the mobile phase A is a monopotassium phosphate buffer, preferably with a concentration of 10 mM and with pH value adjusted to 3.0 with phosphoric acid.

In a certain embodiment, the mobile phase B comprises 10-40%, preferably 20-30%, more preferably 28% of acetonitrile by volume.

In a certain embodiment, the HPLC method comprises a mobile phase gradient. In such embodiments, the relative concentration of mobile phases A and B by volume in the gradient is varied to a gradient of 100% A:0% B to 0% A:100% B run over 5-60 minutes, preferably 10-30 minutes.

In a certain embodiment, an HPLC method for detecting impurities, particularly levomethorphan and norlevelorphanol, in a composition comprising levorphanol tartrate dihydrate has the gradient shown in the table below:

| Time | Mobile Phase A (%) | Mobile Phase B (%) |
| --- | --- | --- |
| 0.00 | 54 | 46 |
| 15.00 | 54 | 46 |
| 25.00 | 20 | 80 |
| 34.00 | 20 | 80 |
| 34.10 | 54 | 46 |
| 39.00 | 54 | 46 |

Preferably, mobile phase A is a phosphate buffer solution, more preferably monopotassium phosphate buffer at pH 3.0, and mobile phase B is a mixture of acetonitrile and methanol, preferably 20-30% acetonitrile by volume.

In another aspect, the invention relates to a method of treating pain in a subject in need thereof. According to embodiments of the invention, such method comprises administering to the subject a composition comprising levorphanol tartrate dihydrate as described herein. Preferably, a subject is a human subject.

In some embodiments, a composition administered to a subject is a pharmaceutical composition further comprising at least one pharmaceutically acceptable carrier. A "carrier" refers to any excipient, diluent, buffer, stabilizer, or other material well known in the art for pharmaceutical formulations. Pharmaceutically acceptable carriers in particular are non-toxic and should not interfere with the efficacy of the active ingredient. Pharmaceutically acceptable carriers can be readily determined by one of ordinary skill in the art, and include excipients and/or additives suitable for use in the pharmaceutical compositions known in the art, e.g., as listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are entirely incorporated herein by reference.

EMBODIMENTS OF THE INVENTION

The invention also provides the following non-limiting embodiments.

Embodiment 1 is a composition comprising levorphanol tartrate dihydrate, in combination with at least one of levomethorphan, and norlevorphanol.

Embodiment 1a is the composition of embodiment 1, comprising levorphanol tartrate dihydrate, levomethorphan, and norlevorphanol.

Embodiment 1b is the composition of embodiment 1, comprising levorphanol tartrate dihydrate and norlevorphanol.

Embodiment 1c is the composition of embodiment 1, comprising levorphanol tartrate dihydrate and levomethorphan.

Embodiment 1d is the composition of embodiment 1, 1a, or 1c, comprising levomethorphan in an amount that is about 0.5% area or less based on peak area of a peak corresponding to levomethorphan as determined by high performance liquid chromatography (HPLC) analysis relative to a total of 100% area based on peak area of peaks corresponding to levorphanol tartrate dihydrate, levomethorphan, and/or norlevorphanol as determined by HPLC analysis.

Embodiment 1e is the composition of embodiment 1, 1a, or 1c, comprising levomethorphan in an amount that is about 0.15% area or less based on peak area of a peak corresponding to levomethorphan as determined by high performance liquid chromatography (HPLC) analysis relative to a total of 100% area based on peak area of peaks corresponding to levorphanol tartrate dihydrate, levomethorphan, and/or norlevorphanol as determined by HPLC analysis.

Embodiment 1f is the composition of any one of embodiments 1, 1a, and 1b, comprising norlevorphanol in an amount that is about 0.5% area or less based on peak area of a peak corresponding to norlevorphanol as determined by high performance liquid chromatography (HPLC) analysis relative to a total of 100% area based on peak area of peaks corresponding to levorphanol tartrate dihydrate, levomethorphan, and/or norlevorphanol as determined by HPLC analysis.

Embodiment 1g is the composition of any one of embodiments 1, 1a, and 1b, comprising norlevorphanol in an amount that is about 0.15% area or less based on peak area of a peak corresponding to norlevorphanol as determined by high performance liquid chromatography (HPLC) analysis relative to a total of 100% area based on peak area of peaks corresponding to levorphanol tartrate dihydrate, levomethorphan, and/or norlevorphanol as determined by HPLC analysis.

Embodiment 1h is the composition of embodiment 1a, comprising each of levomethorphan and norlevorphanol in an amount that is about 0.2% area or less based on a peak area of a peak corresponding to levomethorphan and norlevorphanol, respectively.

Embodiment 1i is the composition of any one of embodiments 1a-1h, comprising levorphanol tartrate dihydrate in an amount that is about 95% area or more, preferably 99.0% area or more, and more preferably 99.5%, 99.6% or 99.7% area or more, based on peak area of a peak corresponding to levorphanol tartrate dihydrate as determined by high performance liquid chromatography (HPLC) analysis relative to a total of 100% area based on peak area of peaks corresponding to levomethorphan, norlevorphanol, and levorphanol tartrate dihydrate, and optionally one or more additional detected impurities as determined by HPLC analysis.

Embodiment 2 is a method of preparing a composition comprising levorphanol tartrate dihydrate, in combination with at least one of levomethorphan and norlevorphanol, the method comprising:
  (i) reacting levorphanol tartrate with a base to obtain a mixture;
  (ii) reacting the mixture with ethyl formate to obtain a second mixture;
  (iii) reacting the second mixture with L-(+)-tartaric acid to obtain a third mixture comprising levorphanol tartrate; and
  (iv) crystallizing the levorphanol tartrate from the third mixture in an aqueous-organic solvent mixture to obtain the composition.

Embodiment 2a is the method of embodiment 2, wherein the levorphanol tartrate in the step (i) is crude levorphanol tartrate.

Embodiment 2a(1) is the method of embodiment 2a, wherein the crude levorphanol tartrate is a product from a reaction between levorphanol and L-(+)-tartaric acid.

Embodiment 2b is the method of embodiment 2, wherein the base in the step (i) is an organic base.

Embodiment 2c is the method of embodiment 2, wherein the base in the step (i) is an inorganic base, preferably sodium carbonate.

Embodiment 2d is the method of embodiment 2, wherein the second mixture in the step (ii) comprises formylated norlevorphanol.

Embodiment 2e is the method of embodiment 2, wherein the third mixture in the step (iii) comprises formylated norlevorphanol.

Embodiment 2f is the method of embodiment 2, wherein the aqueous-organic mixture in the step (iv) comprises a solvent selected from the group consisting of methanol, ethanol, propanol, and isopropyl alcohol.

Embodiment 2f(1) is the method of embodiment 2f, wherein the aqueous-organic mixture in the step (iv) comprises isopropyl alcohol.

Embodiment 3 is a method of determining an amount of at least one impurity in a composition comprising levorphanol tartrate dihydrate, the method comprising:
  (i) dissolving the composition in a suitable solvent to prepare a sample solution;
  (ii) dissolving a reference standard of levorphanol tartrate dihydrate in a solvent to prepare a standard solution;
  (iii) analyzing the sample solution and the standard solution by high performance liquid chromatography (HPLC) to identify a peak corresponding to levorphanol tartrate dihydrate and the at least one impurity;
  (iv) measuring an area of the peak corresponding to levorphanol tartrate dihydrate and an area of the peak corresponding to the at least one impurity; and (v) determining the amount of the at least one impurity based on the peak areas from step (iv).

Embodiment 3a is the method of embodiment 3, wherein the composition further comprises levomethorphan.

Embodiment 3b is the method of embodiment 3, wherein the composition further comprises norlevorphanol.

Embodiment 3c is the method of embodiment 3, wherein the composition further comprises levomethorphan and norlevorphanol.

Embodiment 3d is the method of embodiment 3, wherein the impurity is levomethorphan.

Embodiment 3e is the method of embodiment 3, wherein the impurity is norlevorphanol.

Embodiment 3f is the method of embodiment 3, wherein the impurities are levomethorphan and norlevorphanol.

Embodiment 4 is a composition comprising levorphanol tartrate dihydrate, in combination with at least one of levomethorphan and norlevorphanol, wherein the composition is obtained by a method comprising:
 (i) reacting levomethorphan tartrate with a base to obtain a mixture;
 (ii) reacting the mixture with ethyl formate to obtain a second mixture;
 (iii) reacting the second mixture with L-(+)-tartaric acid to obtain a third mixture comprising levorphanol tartrate; and
 (iv) crystallizing the levorphanol tartrate from the third mixture in an aqueous-organic solvent mixture to obtain the composition.

Embodiment 4a is the composition of embodiment 4, comprising levomethorphan in an amount that is about 0.5% area or less based on peak area of a peak corresponding to levomethorphan as determined by high performance liquid chromatography (HPLC) analysis relative to a total of 100% area based on peak area of peaks corresponding to levorphanol tartrate dihydrate, levomethorphan, and norlevorphanol as determined by HPLC analysis.

Embodiment 4b is the composition of embodiment 4, comprising levomethorphan in an amount that is about 0.15% area or less based on peak area of a peak corresponding to levomethorphan as determined by high performance liquid chromatography (HPLC) analysis relative to a total of 100% area based on peak area of peaks corresponding to levorphanol tartrate dihydrate, levomethorphan, and norlevorphanol as determined by HPLC analysis.

Embodiment 4c is the composition of any one of embodiments 4-4b, comprising norlevorphanol in an amount that is about 0.5% area or less based on peak area of a peak corresponding to norlevorphanol as determined by high performance liquid chromatography (HPLC) analysis relative to a total of 100% area based on peak area of peaks corresponding to levorphanol tartrate dihydrate, levomethorphan, and norlevorphanol as determined by HPLC analysis.

Embodiment 4d is the composition of any one of embodiments 4-4b, comprising norlevorphanol in an amount that is about 0.15% area or less based on peak area of a peak corresponding to norlevorphanol as determined by high performance liquid chromatography (HPLC) analysis relative to a total of 100% area based on peak area of peaks corresponding to levorphanol tartrate dihydrate, levomethorphan, and norlevorphanol as determined by HPLC analysis.

Embodiment 4e is the composition of embodiment 4, comprising each of levomethorphan and norlevorphanol in an amount that is about 0.2% area or less based on a peak area of a peak corresponding to levomethorphan and norlevorphanol, respectively.

Embodiment 4f is the composition of embodiment 4, comprising levorphanol tartrate dihydrate in an amount that is about 95% area or more, preferably 99.0% area or more, and more preferably 99.5%, 99.6% or 99.7% area or more, based on peak area of a peak corresponding to levorphanol tartrate dihydrate as determined by high performance liquid chromatography (HPLC) analysis relative to a total of 100% area based on peak area of peaks corresponding to the composition as determined by HPLC analysis.

Embodiment 4g is the composition of any one of embodiments 4-4f, wherein the levorphanol tartrate in the step (i) is crude levorphanol tartrate.

Embodiment 4g(1) is the composition of embodiment 4g, wherein the crude levorphanol tartrate is a product from a reaction between levorphanol and L-(+)-tartaric acid.

Embodiment 4h is the composition of any one of embodiments 4-4f, wherein the base in the step (i) is an organic base.

Embodiment 4i is the composition of any one of embodiments 4-4f, wherein the base in the step (i) is an inorganic base, preferably sodium carbonate.

Embodiment 4j is the composition of any one of embodiments 4-4f, wherein the second mixture in the step (ii) comprises formylated norlevorphanol.

Embodiment 4k is the composition of any one of embodiments 4-4f, wherein the third mixture in the step (iii) comprises formylated norlevorphanol.

Embodiment 4l is the composition of any one of embodiments 4-4f, wherein the aqueous-organic mixture in the step (iv) comprises a solvent selected from the group consisting of methanol, ethanol, propanol, and isopropyl alcohol.

Embodiment 4l(1) is the composition of any one of embodiments 4-4f, wherein the aqueous-organic mixture in the step (iv) comprises isopropyl alcohol.

Embodiment 5 is a high performance liquid chromatography (HPLC) method for identifying impurities in a sample, the method comprising analyzing the sample by HPLC and identifying a peak corresponding to the at least one impurity, wherein mobile phase A is a phosphate buffer solution, mobile phase B is a mixture of acetonitrile and methanol, and diluent is water.

Embodiment 5a is the HPLC method of embodiment 5, wherein the mobile phase A is a monopotassium phosphate buffer, preferably with a concentration of 10 mM and with pH value adjusted to 3.0 with phosphoric acid.

Embodiment 5b is the HPLC method of embodiment 5 of 5a, wherein the mobile phase B comprises 10-40%, preferably 20-30%, more preferably 28% of acetonitrile by volume.

Embodiment 5c is the HPLC method of embodiment 5, further comprising a mobile phase gradient.

Embodiment 5c(1) is the HPLC method of embodiment 5c, wherein a relative concentration of mobile phase A and B by volume in the gradient is varied to a gradient of 100% A:0% B to 0% A:100% B run over 5-60 minutes, preferably 10-30 minutes.

Embodiment 5d is the HPLC method of embodiment 5, wherein the HPLC method has the gradient shown in the table below:

| Time | Mobile Phase A (%) | Mobile Phase B (%) |
| --- | --- | --- |
| 0.00 | 54 | 46 |
| 15.00 | 54 | 46 |
| 25.00 | 20 | 80 |
| 34.00 | 20 | 80 |

-continued

| Time | Mobile Phase A (%) | Mobile Phase B (%) |
|------|--------------------|--------------------|
| 34.10 | 54 | 46 |
| 39.00 | 54 | 46 |

Embodiment 6 is a method of treating pain in a subject in need thereof, the method comprising administering to the subject the composition of any one of embodiments 1-1f.

Embodiment 6a is the method of embodiment 6, wherein the composition is a pharmaceutical composition further comprising at least one pharmaceutically acceptable carrier.

The following examples are to further illustrate the nature of the invention. It should be understood that the following examples do not limit the invention and that the scope of the invention is determined by the appended claims.

REFERENCES

1. U.S. Pat. No. 2,744,112
2. US 2008/0146805
3. U.S. Pat. No. 2,524,855
4. U.S. Pat. No. 3,634,429
5. U.S. Pat. No. 4,521,601
6. U.S. Pat. No. 4,727,147
7. U.S. Pat. No. 5,892,044
8. Kumuraguru et al. "An Improved Process for the Preparation of (+)-3-methoxy-N-formylmorphinan" Organic Process Research & Development, 2014, 18, 174-178.

EXAMPLES

The following abbreviations and chemical notations are used in the following examples, unless clearly stated otherwise:
THF: tetrahydrofuran
MeTHF: 2-methyltetrahydrofuran
EtOAc: ethyl acetate
IPA: isopropyl alcohol
DCM: methylene chloride
ACN: acetonitrile
LAH: lithium aluminum hydride
HBr: hydrobromic acid
$NH_4OH$: ammonium hydroxide
HPLC: high performance liquid chromatography
$^1H$ NMR: proton nuclear magnetic resonance
$^{13}C$ NMR: carbon nuclear magnetic resonance
m.p.: melting point
LC-MS: liquid chromatography mass spectrometry
TLC: thin layer chromatography
USP water: purified water, which is water obtained by a suitable process according to U.S. Pharmacopeia (USP)

Example 1: Preparation of Formyl-Levomorphan

Otabase Mandelate Salt

Octabase mandelate salt (100 g, 0.24 mol) and 2-methyltetrahydrofuran (300 g) were added to a reactor. Then a solution of sodium carbonate (60 g) in water (540 g) was also added to the reactor. The resulting mixture was stirred at room temperature for 30 minutes. The phases were separated and the aqueous phase was extracted with ethyl formate (300 g). The phases were separated and the organic phases were combined. Additional ethyl formate (200 g) was added to the reactor and the resulting mixture stirred at 57° C.±5° C. (reflux) for about 13 hours. Then the solvent was removed by distillation at 60±10° C. under atmospheric pressure. After distillation, a mixture of poly phosphoric acid (350 g) and sulfuric acid (10 g) was added to the residue, and then additional poly phosphoric acid (350 g) was used for rinse. The resulting mixture was stirred at 50° C.±5° C. for about 72 hours.

The reaction was cooled down to 10° C.±5° C., and then water (700 g) and ethyl acetate (350 g) were added to the reactor. The phases were separated and the aqueous phase was extracted with ethyl acetate (350 g). Organic phases were combined and additional ethyl acetate (100 g) was used for rinse. The combined organic phases were washed with water (210 g) followed by 30% sodium hydroxide (50 g) in water (110 g plus 50 g for rinse) followed by water (210 g) to obtain a solution of formyl-levomethorphan in ethyl acetate.

Example 2: Preparation of Levorphanol Tartrate

Formyl-Levomethorphan

A solution of 100 g of formyl-levomethorphan (prepared as described in Example 1) in ethyl acetate was added to a reactor, and then was distilled at 50° C.±10° C. under vacuum to a minimum stir volume. Then 2-methyltetrahydrofuran (MeTHF, 760 g) was added to the residue and the resulting mixture was distilled again at 50° C.±10° C. under vacuum to a minimum stir volume. The residue was charged with MeTHF (670 g) and cooled to 0-10° C.

A solution of lithium aluminum hydride (LAH) in tetrahydrofuran (THF) (200 g) was slowly added to the reactor while maintaining an internal temperature of no more than 30° C. The resulting mixture was stirred at 0-10° C. for 1 hour and then at 6-70° C. for 1 hour. After the reaction was completed, the reaction mixture was cooled to 0-10° C. Then a premixed mixture of water (100 g) and 30% sodium hydroxide (14 g) was slowly charged to the reactor while maintaining an internal temperature of no more than 30° C. The resulting mixture was then stirred for 1 hour and then filtered. The filter cake was washed twice with MeTHF (200 g, 200 g). The filtrate and cake washes were transferred back to a clean reactor and rinse forward with MeTHF (100 g). The mixture was washed with water (300 g) and the aqueous phase was discarded.

The remaining reactor contents were distilled under vacuum down to minimum stir volume. Acetonitrile (ACN, 500 g) was added and the mixture was heated to dissolve solids if present. The resulting mixture was distilled again under vacuum down to minimum stir volume followed by addition of ACN (300 g). The mixture was heated to 70-80° C. to dissolve solids if present and then was cooled down to 0-10° C. over 10 hours. Then the mixture was hold at 0-10° C. for about 3 hours. The slurry was filtered to collect the solid. The filter cake was washed with ACN (100 g) followed by water (200 g). The filtered solid was then dissolved in hydrobromic acid (HBr, 450 g) and transferred back to a reactor. The filter was rinsed into the reactor with additional HBr (110 g). The resulting mixture was stirred at 90-100° C. until reaction completion. Isopropyl alcohol (IPA, 280 g), methylene chloride (DCM, 280 g), 28% ammonium hydroxide ($NH_4OH$, 740 g) and water (160 g) were premixed in a second reactor at 0-10° C. The mixture in the first reactor was slowly charged into the second reactor containing $NH_4OH$ while keeping a temperature of no more than 30° C. The phases were agitated and separated. Then the aqueous phase was extracted with a mixture of IPA (280g) and DCM (280g). The organic phases were combined and rinsed forward with IPA (80g). The resulting organic mixture was washed twice with $NH_4OH$ (240 g, 240 g), and was rinsed forward with IPA (80 g, 80 g).

The resulting organic mixture was distilled under vacuum to minimum stir volume and then was charged with IPA (1000 g). Then the mixture was heated to dissolve solids if present. The resulting IPA solution was filtered through a polish filter, and the filtrate was distilled under vacuum to a target volume of 6.5-8 liters per kilogram of levorphanol, and was carried to the next step.

A solution of L-(+)-tartaric acid (87 g) in water (87 g) was premixed, and then was charged to the levorphanol solution in IPA while keeping temperature no less than 50° C. The resulting mixture was stirred for about 30 minutes at 60-70° C., cooled to 10-20° C. over 8 hours, and then held at 10-20° C. for about 8 hours. The mixture was filtered to collect the solid and the filter cake was washed with a mixture of IPA (150 g) and water (7 g) followed by another mixture of IPA (100 g) and water (5 g). The filter cake was dried to obtain about 92 g of crude levorphanol tartrate as white crystalline solid (typical molar yield of 45%-55% and mass yield of 60% to 70%).

Example 3: Purification of Levorphanol Tartrate

Crude levorphanol tartrate (100 g) obtained according to Example 2, and 2-methyltetrahydrofuran (210 g) were charged to a reactor, followed by addition of a solution of sodium carbonate (40 g) in water (110 g). The resulting mixture was stirred at a temperature of 50° C.±5° C. for 30 minutes. The phases were separated and the aqueous phase was extracted with ethyl formate (300 g). The organic phases were combined. Additional ethyl formate (200 g) was charged and the resulting mixture was heated at 57° C.±5° C. The reaction was monitored by HPLC for completion, which was usually completed within about 4 hours of heating. After the reaction was completed, the resulting mixture was distilled under reduced pressure down to minimum stir volume. The residue was charged with IPA (1000 g) and the resulting mixture was heated to dissolve solids if present.

The resulting IPA solution was filtered through polish filter and rinsed forward with IPA (200 g). The resulting mixture was distilled under reduced pressure down to a target volume of about 725 ml. The remaining mixture was heated to dissolve solids if present, and then was charged with a premixed solution of L-(+)-tartaric acid (87 g) in water (87 g) while keeping a temperature of no less than 50° C. The resulting mixture was stirred for about 30 minutes at 60-70° C., cooled to 10-20° C. over 8 hours, and held at 10-20° C. for about 8 hours. The solids were isolated by filtration, and the filter cake was washed with a mixture of IPA (150 g) and water (7 g) followed by another mixture of IPA (100 g) and water (5 g). Dry filter cake to obtain about 85 g of levorphanol tartrate as white crystalline solid (typical yield of 80% to 90%).

Example 4: Preparation of Levorphanol Tartrate Dihydrate

Levorphanol tartrate

Levorphanol tartrate dihydrate

Levorphanol tartrate (100g) and USP water (450 g) were charged to a reactor, and the resulting mixture was heated until dissolved with addition of USP water (100g). The solution is filtered through a polish filter and the lines were rinsed with USP water (100 g). The resulting solution was distilled under vacuum to about 450 ml. The resulting solution was heated at 85-95° C. for approximately 30 minutes. The mixture was stirred while being cooled over about 4 hours to approximately 10-20° C., and was held for another 2 hours at 10-20° C. while being milled. The solids were isolated by filtration and the wet cake was washed three times with USP water (150 g, 150, and 100g).

The obtained solid and USP water (405 g) were charged to a reactor, and the resulting mixture was heated to dissolve with addition of USP water (90 g). The resulting solution was distilled under vacuum to about 400 ml. The remaining solution was then heated at 85-95° C. for approximately 30 minutes, and cooled to 65-75° C. Seeds of levorphanol tartrate (0.09 g) were added to the mixture. The resulting mixture was stirred at 85-95° C. for approximately 30 minutes and then was cooled over about 4 hours to approximately 10-20° C. The slurry was then milled for about 4 hours at 10-20° C. and held for about 2 hours at 10-20° C. while being milled. The solids were isolated by filtration and the wet cake was washed three times with USP water. The solids were dried at 35-45° C. to obtain about 82 g of levorphanol tartrate dihydrate as white crystalline solid (typical molar yield of 65%-75% and mass yield of 71%-82%).

Example 5: HPLC Analysis of Compositions Comprising Levorphanol Tartrate Dihydrate Reagents and Materials The following equipment and reagents are required. Equivalent equipment or reagents may be substituted:
Liquid chromatographic system equipped with a sample injector, photodiode array (PDA) detector or a variable wavelength detector, and electronic integrator;
Chromatographic column: Kromasil C18, 250×4.6 mm, 5 µm particle size, 100 A Phenomenex;
P/N:00G-3033-E0, or Kromasil, P/N M05CLA25, or equivalent;
0.45 um Nylon filter;
Water: HPLC Grade, or equivalent;
Potassium Phosphate monobasic: HPLC Grade, or equivalent;
Octane sulfonic acid sodium salt monohydrate: HPLC grade or equivalent;
Phosphoric acid: ACS Reagent;
Acetonitrile (ACN): HPLC Grade, or equivalent;
Methanol (MeOH): HPLC Grade, or equivalent;
Volumetric flasks (Class A) and sample vials;
Analytical balance capable of accurately weighing to the nearest 0.01 mg;
Levorphanol Tartrate Dihydrate: Reference Standard; and
Levomethorphan: Reference Standard.

Chromatographic Conditions

Figure 1:
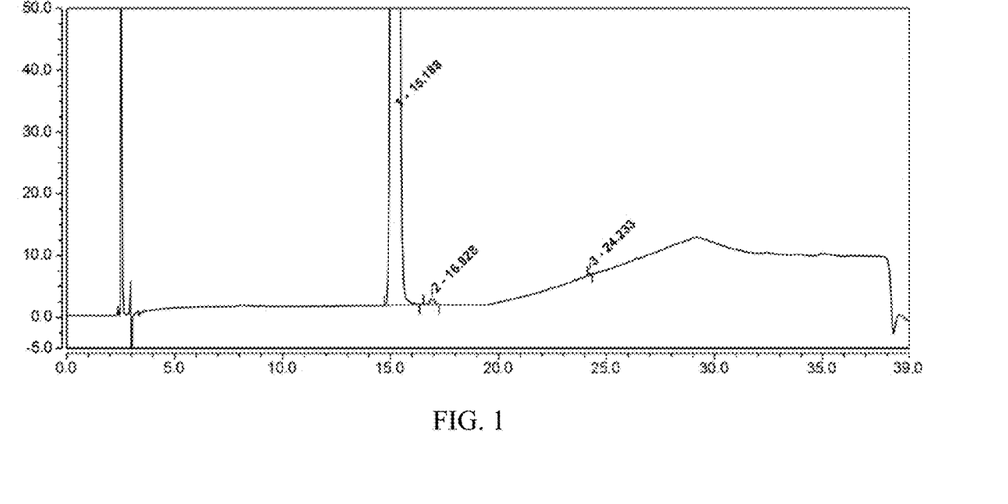
FIG. 1 is a sample HPLC chromatogram of a standard injection of levorphanol tartrate dihydrate as described in Example 5, which shows the peak of levorphanol tartrate dihydrate at 15.2 minutes, the peak of norlevorphanol at 16.9 minutes, and the peak of levomethorphan at 24.2 minutes.
Figure 2:
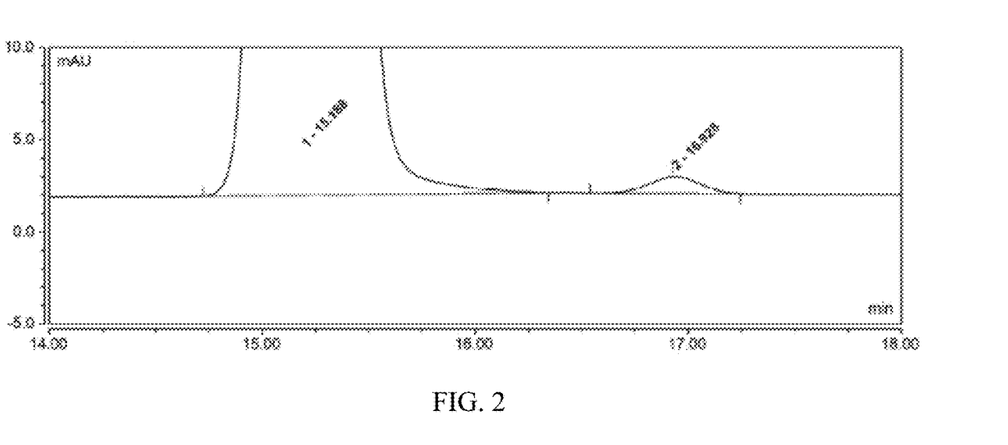
FIG. 2 is an expanded view of the sample HPLC chromatogram of the standard injection shown in FIG. 1.
Figure 3:
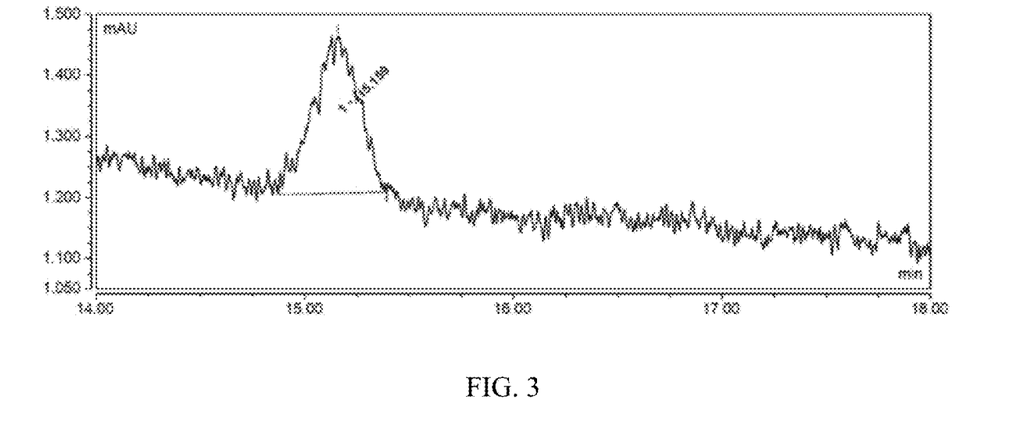
FIG. 3 is an expanded view of a sample HPLC chromatogram of a sensitivity injection, as described in Example 5 which shows the peak of levorphanol tartrate dihydrate at 15.2 minutes.
Figure 4:
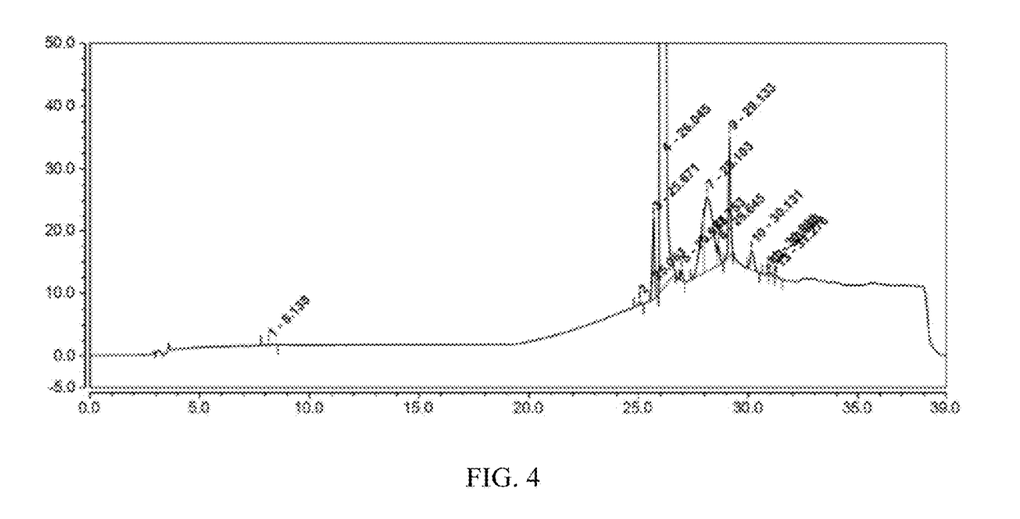
FIG. 4 is an expanded view of a sample HPLC chromatogram of levomethorphan, which shows the peak of levomethorphan at 26.0 minutes and the peak of formyl-levomethorphan at 30.1 minutes.
Figure 5:
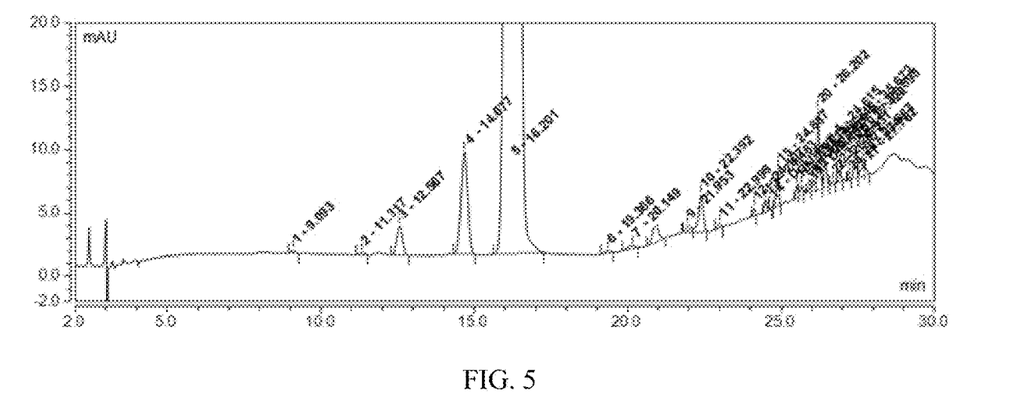
FIG. 5 is a sample HPLC chromatogram of a standard injection of norlevorphanol, which shows the peak of levorphanol at 14.7 minutes and the peak of norlevorphanol at 16.2 minutes.

Sample HPLC chromatograms are shown in FIGS. 1-4.

Mobile Phase and Diluent Preparation

Mobile Phase A (10 mM Monopotassium Phosphate buffer solution pH 3.0): 1.36 g of potassium phosphate monobasic and 1.08 g of octane sulfonic acid sodium salt were weighed and transferred into a 1 L bottle, followed by addition of 1000 mL of water. The resulting mixture was mixed well to dissolve and adjust the pH of the buffer solution with phosphoric acid to pH 3.0. The resulting solution was filtered with 0.45 um filter.

Mobile Phase B (28:72 Acetonitrile:Methanol):

Acetonitrile (280 mL) and methanol (720 mL) were transferred into a 1 L bottle. The resulting mixture was mixed well.

Diluent: 100% Water

HPLC Operating Parameters

Mobile Phase Gradient:

| Time | A % | B % |
| --- | --- | --- |
| 0.00 | 54 | 46 |
| 15.00 | 54 | 46 |
| 25.00 | 20 | 80 |
| 34.00 | 20 | 80 |
| 34.10 | 54 | 46 |
| 39.00 | 54 | 46 |

Column: Kromasil C18, 250×4.6 mm, 5 μm particle size, 100 A
Run Time: 39 min
Flow Rate: 0.8 mL/min
Detection: UV at 224 nm
Injection Volume: 10 μL
Column Temperature: 40° C.
Autosampler Temperature: Ambient
Needle Wash: 50:50, MeOH:Water
Levorphanol tartrate dihydrate Retention Time: about 15.1 minutes
Levomethorphan Retention Time: about 26.0 minutes Preparation of Standard and Sample Solutions Levomethorphan Retention Time (RT) Solution:

50 mg of levomethorphan was weighed and transferred into a 50 mL volumetric flask, followed by addition of 25 mL of acetonitrile and sonication. The mixture was diluted to volume with diluent and mixed well.

Standard Solution (1.0 mg/mL):

Levorphanol tartrate (20 mg) was weighed and transferred into a 20 mL volumetric flask, and the resulting mixture was diluted to volume with diluent. This standard solution was prepared in duplicate, each labelled as "Standard Solution A" and "Standard Solution B", respectively.

Impurity Standard Solution (1.0% nominal, 0.01 mg/mL):

1.0 mL of Standard Solution A was transferred into a 100 mL volumetric flask and then diluted to volume with diluent and mixed well.

Sensitivity Solution (0.05% nominal, 0.5 μg/mL):

1.0 mL of Impurity Standard Solution was transferred into a 20 mL volumetric flask and then diluted to volume with diluent.

Sample Solution:

25 mg of sample was weighed and transferred into a 25 mL volumetric flask. Diluent was added to volume to dissolve the sample. The sample solution was prepared in duplicate.

Injection Sequence:

An example injection sequence is shown in the table below. Every 8 or fewer injections of samples are bracketed with injections of Standard Solution A and Impurity Standard Solution to verify that the HPLC conditions are suitable for use. Bracketing standards are injections of reference standard solution to confirm that retention times remain consistent and peak shapes are appropriate.

TABLE 1

Example of Injection Sequence

| Solution | # of Injections |
| --- | --- |
| Diluent | 2 or more |
| Sensitivity Solution | 1 |
| Levomethorphan RT solution | 1 |
| Standard Solution B | 1 |
| Standard Solution A | 6 |
| Impurity Standard | 1 |
| Sample Solutions for analysis | Up to 8 |
| Standard Solution A | 1 |
| Impurity Standard | 1 |

Calculations

Identity of Levorphanol:

The retention time of the main peak in the Sample Solutions was compared with the retention time of the Levorphanol peak from the closest injection of Standard Solution A. The retention time in the sample solution must be within ±2.0% of the Standard Solution.

Assay of Levorphanol Tartrate:

The assay of Levorphanol Tartrate (as-is) was calculated as follows:

$$\text{Assay (wt \%)} = \frac{A_{Sam}}{A_{Std}} \times \frac{C_{Std} \times ((100 - KF_{Std})/100) \times PF}{C_{Sam} \times ((100 - KF_{Sam})/100)} \times 100$$

Where:
$A_{Sam}$=The peak area of Levorphanol in the injection of Sample Solution.
$A_{Std}$=The average peak area of Levorphanol in the bracketing injections of Standard Solution A.
$C_{Sam}$=Concentration of the Sample Solution, in mg/mL
$C_{Std}$=Concentration of Standard Solution A, in mg/mL, adjusted for purity
PF=Purity Factor, refer to Reference Standard CofA
$KF_{Sam}$=Water content of the sample
$KF_{Std}$=Water content of the standard Note: The assay calculation below assumes the use of the dihydrate form USP Levorphanol Tartrate reference standard. The calculations will need to be adjusted accordingly when using other standard forms.

Individual Impurity Content Determination:

The impurities present were identified by noting the relative retention times (RRT) of the observed secondary peaks, discounting any peaks not related to the sample.

$$RRT = \frac{\text{Retention Time of the Secondary Peak}}{\text{Retention Time of the Levorphanol Peak}}$$

The percentage of individual impurities from each sample solution injection was calculated using the following formula:

$$\text{Impurity(\%)} = \frac{A_{Sam}}{A_{ImpStd}} \times \frac{C_{Std} \times ((100 - KF_{Std})/100) \times PF}{C_{Sam} \times ((100 - KF_{Sam})/100)} \times 100$$

Where:
$A_{ImpStd}$=The average peak area of Levorphanol in the bracketing injections of Impurity Standard Solution.

Total Impurity Content Determination:

The average of each individual impurity was determined as discussed above. The total impurities was calculated by summing the average level of each individual impurity≥0.05%.

Impurity Determination:

The purity of Levorphanol Tartrate Dihydrate samples were calculated as follows:

Purity (%)=100−Total Impurities

Analysis Results:

The specification of levorphanol tartrate dihydrate is as follows:
1. The retention time of the sample is consistent with that of the reference standard;
2. The assay by HPLC shows that the sample contain 98.0%-102.0% of levorphanol tartrate dihydrate, which is calculated on the anhydrous basis;
3. The assay by titration shows that the sample contains 99.0%-101.0% of levorphanol tartrate dihydrate, which is calculated on the anhydrous basis;
4. Impurity level by HPLC: no more than 0.20% of levomethorphan, and no more than 0.20% of norlevorphanol;
5. Chiral impurity level by HPLC: no more than 0.15% of dextrophan tartrate;
6. Any one of individual HPLC impurity is no more than 0.10%.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of preparing a composition comprising levorphanol tartrate dihydrate in an amount of 99.80% or greater and norlevorphanol in an amount of 0.20% or less, the method comprising:
    (i) reacting levorphanol tartrate with a base to obtain a mixture;
    (ii) reacting the mixture with ethyl formate to obtain a second mixture;
    (iii) reacting the second mixture with L-(+)-tartaric acid to obtain a third mixture comprising levorphanol tartrate; and
    (iv) crystallizing the levorphanol tartrate from the third mixture in an aqueous-organic solvent mixture to obtain the composition.

2. The method of claim 1, wherein the aqueous-organic mixture in the step (iv) comprises a solvent selected from the group consisting of methanol, ethanol, propanol, and iso-propyl alcohol, or a mixture thereof.

3. The method of claim 1, wherein the composition comprises norlevorphanol in an amount of 0.1% or less.

4. The method of claim 1, further comprising determining an amount of levomethorphan and norlevorphanol by a method comprising:
    (i) dissolving the composition in a suitable solvent to prepare a sample solution;
    (ii) dissolving a reference standard of levorphanol tartrate dihydrate in a solvent to prepare a standard solution;
    (iii) analyzing the sample solution and the standard solution by high performance liquid chromatography (HPLC) to identify a peak corresponding to each of levorphanol tartrate dihydrate, and norlevorphanol;
    (iv) measuring an area of each HPLC peak;
    (v) determining the amount of norlevorphanol based on the area from step (iv).

* * * * *